US011602300B2

(12) United States Patent
Zhang et al.

(10) Patent No.: US 11,602,300 B2
(45) Date of Patent: Mar. 14, 2023

(54) BRAIN-COMPUTER INTERFACE BASED ROBOTIC ARM SELF-ASSISTING SYSTEM AND METHOD

(71) Applicant: South China University of Technology, Guangzhou (CN)

(72) Inventors: Zhijun Zhang, Guangzhou (CN); Yongqian Huang, Guangzhou (CN); Yuanqing Li, Guangzhou (CN)

(73) Assignee: South China University of Technology, Guangzhou (CN)

( * ) Notice: Subject to any disclaimer, the term of this patent is extended or adjusted under 35 U.S.C. 154(b) by 929 days.

(21) Appl. No.: 16/471,505

(22) PCT Filed: Oct. 11, 2017

(86) PCT No.: PCT/CN2017/105622
§ 371 (c)(1),
(2) Date: Jun. 19, 2019

(87) PCT Pub. No.: WO2018/113392
PCT Pub. Date: Jun. 28, 2018

(65) Prior Publication Data
US 2019/0387995 A1 Dec. 26, 2019

(30) Foreign Application Priority Data

Dec. 20, 2016 (CN) .......................... 201611180477.8

(51) Int. Cl.
*G06F 17/00* (2019.01)
*A61B 5/375* (2021.01)
(Continued)

(52) U.S. Cl.
CPC ................. *A61B 5/375* (2021.01); *B25J 3/04* (2013.01); *B25J 13/087* (2013.01);
(Continued)

(58) Field of Classification Search
CPC . A61B 5/375; B25J 3/04; B25J 13/087; B25J 9/1689; B25J 13/00; B25J 9/1682;
(Continued)

(56) References Cited

U.S. PATENT DOCUMENTS 5,465,729 A * 11/1995 Bittman ................. A61B 5/375
600/545
6,537,301 B1 * 3/2003 Kamei ................. A61N 5/0618
607/88
(Continued)

FOREIGN PATENT DOCUMENTS

CN 1927551 A 3/2007
CN 102198660 A 9/2011
(Continued)

OTHER PUBLICATIONS

Brain-Controlled Robotic Arm System Based on Multi-Directional CNN-BiLSTM Network Using EEG Signals (Year: 2020).*
(Continued)

*Primary Examiner* — Ronnie M Mancho
(74) *Attorney, Agent, or Firm* — The Dobrusin Law Firm, PC (57) ABSTRACT

Disclosed are a brain-computer interface based robotic arm self-assisting system and method. The system comprises a sensing layer, a decision-making layer and an execution layer. The sensing layer comprises an electroencephalogram acquisition and detection module and a visual identification and positioning module and is used for analyzing and identifying the intent of a user and identifying and locating positions of a corresponding cup and the user's mouth based on the user intent. The execution layer comprises a robotic arm control module that performs trajectory planning and control for a robotic arm based on an execution instruction received from a decision-making module. The decision-making layer comprises the decision-making module that is
(Continued)

connected to the electroencephalogram acquisition and detection module, the visual identification and positioning module and the robotic arm control module to implement the acquisition and transmission of data of an electroencephalogram signal, a located position and a robotic arm status and the sending of the execution instruction for the robotic arm. The system combines the visual identification and positioning technology, a brain-computer interface and a robotic arm to facilitate paralyzed patients to drink water by themselves, improving the quality of life of the paralyzed patients.

10 Claims, 4 Drawing Sheets

(51) Int. Cl.
　　B25J 3/04　　　(2006.01)
　　B25J 13/08　　　(2006.01)
　　G05B 19/4097　　(2006.01)
　　G06F 3/01　　　(2006.01)
　　H04W 80/06　　　(2009.01)

(52) U.S. Cl.
　　CPC ......... *G05B 19/4097* (2013.01); *G06F 3/015* (2013.01); *H04W 80/06* (2013.01); *G05B 2219/35444* (2013.01); *G05B 2219/39451* (2013.01)

(58) Field of Classification Search
　　CPC .............. B25J 9/1664; G05B 19/4097; G05B 2219/35444; G05B 2219/39451; G05B 2219/40413; G06F 3/015; G06F 3/013; G06F 3/0304; G06F 3/0482; G06F 2203/011; H04W 80/06
　　USPC .......................................................... 600/545
　　See application file for complete search history.

(56) References Cited

U.S. PATENT DOCUMENTS

| | | | | |
|---|---|---|---|---|
| 6,682,182 | B2 * | 1/2004 | Jeanmaire | B41J 2/07 347/74 |
| 8,483,816 | B1 * | 7/2013 | Payton | A61B 34/30 700/245 |
| 8,579,795 | B2 * | 11/2013 | Martel | A61M 21/02 347/135 |
| 9,389,685 | B1 * | 7/2016 | Pathirage | H04N 5/225 |
| 9,405,366 | B2 * | 8/2016 | Segal | G06F 16/436 |
| 9,445,739 | B1 * | 9/2016 | Payton | G06F 3/015 |
| 9,468,541 | B2 * | 10/2016 | Contreras-Vidal | A61B 5/316 |
| 10,195,058 | B2 * | 2/2019 | Katyal | A61F 2/72 |
| 10,507,157 | B2 * | 12/2019 | Vaillant | G06F 1/163 |
| 10,589,087 | B2 * | 3/2020 | Tyler | G06F 3/012 |
| 10,603,545 | B2 * | 3/2020 | Macri | G09B 19/003 |
| 2003/0181961 | A1 * | 9/2003 | Kamei | A61M 21/00 607/88 |
| 2007/0239063 | A1 * | 10/2007 | Narfstrom | A61B 5/398 600/558 |
| 2009/0221928 | A1 * | 9/2009 | Einav | A61B 5/4076 601/5 |
| 2010/0094156 | A1 | 4/2010 | Collura | |
| 2013/0211592 | A1 | 8/2013 | Kim | |
| 2013/0303837 | A1 * | 11/2013 | Berka | A61B 5/389 600/27 |
| 2014/0058528 | A1 * | 2/2014 | Contreras-Vidal | A61B 5/291 600/383 |
| 2014/0188311 | A1 * | 7/2014 | Masson | B64D 10/00 701/3 |
| 2014/0303428 | A1 * | 10/2014 | Berka | A61B 5/6803 600/27 |
| 2014/0336781 | A1 * | 11/2014 | Katyal | A61F 2/72 623/25 |
| 2016/0235323 | A1 * | 8/2016 | Tadi | A61B 5/1128 |
| 2016/0338611 | A1 * | 11/2016 | Kalinin | A61B 5/6805 |
| 2018/0235833 | A1 * | 8/2018 | Vaillant | G09B 21/003 |
| 2018/0239430 | A1 * | 8/2018 | Tadi | G06F 3/015 |
| 2019/0201691 | A1 * | 7/2019 | Poltorak | A61M 21/02 |
| 2019/0224441 | A1 * | 7/2019 | Poltorak | G06F 3/015 |
| 2019/0387995 | A1 * | 12/2019 | Zhang | G06F 3/015 |

FOREIGN PATENT DOCUMENTS

| | | | | |
|---|---|---|---|---|
| CN | 105078450 | A | | 11/2015 |
| CN | 204971277 | U | | 1/2016 |
| CN | 105425963 | A | | 3/2016 |
| CN | 105710885 | A | * | 6/2016 ............ B25J 11/008 |
| CN | 105710885 | A | | 6/2016 |
| CN | 106020470 | A | | 10/2016 |
| CN | 106074021 | A | | 11/2016 |
| CN | 106671084 | A | | 5/2017 |
| CN | 109366508 | A | * | 2/2019 |
| CN | 109992113 | B | * | 5/2020 |
| CN | 109605385 | B | * | 12/2020 ............ B25J 11/009 |
| EP | 0861475 | A1 | | 9/1998 |
| WO | 97/20280 | | | 6/1997 |

OTHER PUBLICATIONS

Trajectory Decoding of Arm Reaching Movement Imageries for Brain-Controlled Robot Arm System ; (Year: 2019).*

* cited by examiner

BRAIN-COMPUTER INTERFACE BASED ROBOTIC ARM SELF-ASSISTING SYSTEM AND METHOD

TECHNICAL FIELD

The present invention relates to the field of brain-computer interface application research, and in particular relates to a brain-computer interface based robotic arm self-assisting system and method.

BACKGROUND ART

There are many seriously paralyzed patients in the world who can only do some of the activities necessary for daily life, such as drinking water, by getting help from others. With the continuous development of the artificial intelligence and robot technology, and more and more research findings have been applied to assist such people in order to improve their quality of life, in which the field of Brain Computer Interface (BCI), as one branch of the field of neural engineering, is developing rapidly and has a wide prospect, which has aroused people's research upsurge in the field of brain-computer interface.

Brain-computer interface (BCI) is a new human-machine interaction technique that enables direct communication between a human brain and a computer without the conventional brain output pathway (peripheral nerves and muscle tissues), providing paralyzed patients with a new way to exchange and control information with the outside world. The BCI system may be an invasive system or a non-invasive system, the invasive system will implant electrodes into the skull, and the non-invasive system will only collect scalp electroencephalogram signals. Since the non-invasive brain-computer interface has no need for surgery and is safer and simpler than an invasive system. With the continuous improvement of signal processing methods and techniques, the processing of scalp electroencephalogram (EGG) has reached a certain level, so that it is possible for the brain-computer interface to come into practical application in life. The present invention uses a non-invasive brain-computer interface technique.

At present, some existing researches have attempted to combine the brain-computer interface technique with a robot technique. In the Chinese patent application with the publication number CN 102198660 A, entitled "A brain-machine interface based robotic arm control system and action command control scheme (基于脑-机接口的机械手臂控制系统及动作命令控制方案)", in which a brain-computer interface based on motor imagery realizes control by eight commands, including moving up, moving down, moving left, moving right, moving forward, moving backward, finger grasp and finger release, of the robotic arm. The Chinese patent application with the publication number CN 102309365 A, entitled "A wearable brain-controlled intelligent prosthesis (一种可穿戴的 脑控智能假肢)", realizes wearable detection and calculation for electroencephalogram detection and identification, and combines with the intelligent sensing technique to achieve precise adaptive intelligent control for a prosthesis, so as to improve the efficiency and accuracy of movement of the prosthesis and ideally implement the functions of a human hand. In the Chinese invention patent with the publication number CN 105425963 A, entitled "A system of electroencephalogram-controlled robotic arm (一种脑电波控制机 械臂的系统)", electroencephalogram signals are used to acquire parameters of attention and relaxation to implement preset movements of a robotic arm.

In the invention patents described above, only some simple or even preset robotic arm movement controls are implemented through electroencephalogram signals, which does not take full use of the features and advantages of the combination of the brain-computer interface and the robotic arm self-determination control technique. The brain-computer interface based robotic arm self-assisting system and method can combine the advantages of both the brain-computer interface and the robotic arm, and better utilize the brain-computer interface to improve the quality of life of paralyzed patients and improve their ability to live independently.

SUMMARY OF THE INVENTION

In view of the above deficiencies of the prior art, an object of the present invention is to provide a brain-computer interface based robotic arm self-assisting system.

Another object of the present invention is to provide a brain-computer interface based robotic arm self-assisting method.

The object of the present invention can be achieved by the following technical solution:

a brain-computer interface based robotic arm self-assisting system, which is set up based on a three-layer structure including a sensing layer, a decision-making layer and an execution layer, wherein the sensing layer comprises an electroencephalogram acquisition and detection module and a visual identification and positioning module, the electroencephalogram acquisition and detection module being used for acquiring an electroencephalogram signal and analyzing and identifying the intent of a user, and the visual identification and positioning module being used for identifying and locating positions of a corresponding cup and the user's mouth based on the user intent; the execution layer comprises a robotic arm control module, which is a carrier assisting in operation of a person in practice and performs trajectory planning and control for a robotic arm based on an execution instruction received from a decision-making module; and the decision-making layer comprises a decision-making module, which is connected to the electroencephalogram acquisition and detection module, the visual identification and positioning module and the robotic arm control module to implement acquisition and transmission of data, such as an electroencephalogram signal, a located position and a robotic arm status, and the sending of the execution instruction for the robotic arm.

Preferably, the electroencephalogram acquisition and detection module comprises an electrode cap for electroencephalogram acquisition, an electroencephalogram acquisition device and a first computer, wherein ten channels of "A1", "T5", "P3", "PZ", "P4", "T6", "O1", "Oz", "O2" and "A2" in the electrode cap are used and disposed at positions according to an international standard 10-20 system; and the first computer is used to implement P300 signal detection and a flickering visual stimulation of a function key in the screen, and the function keys for the flickering visual stimulation are regularly distributed in a 2*2 array in the computer screen, including function keys of "cup1", "cup2", "cup3" and "back", and flicker at an interval of 200 ms with change in black and green colors in a random sequence.

Preferably, the visual identification and positioning module comprises two Microsoft Kinect vision sensors and a second computer, wherein the two Microsoft Kinect vision sensors are respectively disposed in front of a cup to be taken and in front of a user for identification and positioning of the cup to be taken and the user's mouth; and the second computer is used to implement a cup contour detection algorithm, a cup positioning algorithm, a template matching and identification algorithm, and a mouth identification and positioning algorithm.

Preferably, the decision-making module implements, based on a TCP communication protocol, acquisition and transmission of data of an electroencephalogram intent, a located position and a robotic arm status and the sending of an execution instruction for the robotic arm by defining unified transmission data variables, including a user's electroencephalogram intent and the information of positions of the cup and the mouth and setting up a service code framework for a client and a server.

Preferably, the robotic arm control module uses a multi-degree-of-freedom robotic arm as an effector.

Another object of the present invention can be achieved by the following technical solution:

a brain-computer interface based robotic arm self-assisting method, comprising the steps as follows:

1) a user is sitting in front of a screen of a first computer, adjusts the position thereof, wears an electrode cap for electroencephalogram acquisition, opens an electroencephalogram acquisition device and the first computer, and confirms that the signal acquisition status is good;

2) a brain-computer interface based robotic arm self-assisting system is started to confirm that the Microsoft Kinect vision sensor used for identifying and locating the user's mouth can correctly capture the user's mouth, and confirm that three preset cups to be taken are correctly placed in the field of view of the Microsoft Kinect vision sensor used for identifying and locating the cups to be taken;

3) the screen of the first computer enters a function key interface of flickering visual stimulation, the function key interface comprising four function keys of "cup1", "cup2", "cup3" and "back";

4) the user gazes at one of the three function keys "cup1", "cup2" or "cup3", that is, selecting one of the three preset cups, and once the function key is selected, the electroencephalogram intent of the user about the selection of the cup is obtained and sent to the visual identification and positioning module and the decision-making module;

5) the visual identification and positioning module identifies and locates the position of the corresponding cup and the position of the user's mouth based on the electroencephalogram intent in the step 4) and sends, based on the TCP communication protocol, the information of the positions of the cup selected by the user and the user's mouth to the decision-making module;

6) the decision-making module generates a corresponding execution instruction for the robotic arm based on the information of the positions of the cup and the user's mouth obtained in the step 5) and the electroencephalogram intent obtained in the step 4), and sends the corresponding execution instruction for the robotic arm to the robotic arm control module;

7) the robotic arm control module performs trajectory planning based on the execution instruction for the robotic arm and controls, based on the planned trajectory, the robotic arm to take the cup selected by the user and transfer the cup to the user's mouth;

8) after drinking water, the user gazes at the function key "back", and once the function key is selected, the user's electroencephalogram intent about returning the cup will be obtained and sent to the decision-making module;

9) the decision-making module generates, based on the electroencephalogram intent for returning the cup obtained in the step 8), a corresponding execution instruction for the robotic arm and sends execution instruction for the robotic arm to the robotic arm control module; and 10) the robotic arm control module performs trajectory planning based on the execution instruction for the robotic arm and controls, based on the planned trajectory, the robotic arm to return the cup selected by the user to the original position and restore the initial position status of the robotic arm, so as to realize the self-assisting function of the robotic arm for assisting the user to drink water.

Preferably, selecting the function keys in the steps 4) and 8) is specifically implemented by the following process: the user gazes at a certain function key in the function key interface of the first computer, the electroencephalogram signal is acquired, amplified, filtered and processed by analog-to-digital conversion through an electrode cap and an electroencephalogram acquisition device, then the data is transferred to the first computer for P300 signal detection, and then the selection of the certain function key is implemented, the P300 signal detection being specifically implemented by the steps of:

(I) processing the EEG signal by 0.1-20 Hz bandpass filtering and noise reduction; and (II) intercepting, with the amplitude of the EEG signal as a feature, data of a time window of 600 ms after a P300 function key flickers, and performing status classification using a Bayesian model, thereby realizing the P300 signal detection.

Preferably, in the step 5), identifying and locating the position of the corresponding cup is specifically implemented by the steps of:

(1) extracting the horizontal plane in which the cup is placed in the three-dimensional point cloud of the Microsoft Kinect vision sensor through a region growing algorithm;

(2) removing the horizontal plane extracted in the step (1), and performing extraction and segmentation for the object from the remaining three-dimensional point cloud;

(3) respectively matching, using a template matching algorithm, the color image corresponding to each object point cloud set obtained in the step (2) with preset images in a library to identify the point cloud set corresponding to the cup selected by the user; and (4) performing average calculation for the point cloud set corresponding to the selected cup obtained in the step (3) so that the positioning for the cup in a coordinate system of the Microsoft Kinect vision sensor is implemented and converted into the positioning in a robotic arm coordinate system.

Preferably, in the step 5), identifying and locating the position of the user's mouth is specifically implemented by the steps of: performing human body detection using a software development kit provided by the Microsoft Kinect vision sensor itself so that a coordinate position of the user's mouth in a coordinate system of the Microsoft Kinect vision sensor is acquired and converted into coordinate positions in a robotic arm coordinate system.

Preferably, in the steps 7) and 10), performing trajectory planning and control for the robotic arm is specifically implemented by the process of: combining preset key trajectory points with coordinate points of the user's mouth and the selected cup in the robotic arm coordinate system to plan an operation trajectory of the robotic arm, and calling the corresponding API of the robotic arm to control the robotic arm to operate based on the planned trajectory, so as to realize the self-assisting function of the robotic arm for assisting the user to drink water.

As compared with the prior art, the present invention has the following advantages and beneficial effects:

1. In the present invention, based on the combination of the P300-based brain-computer interface technique and the assisting technique of a robotic arm with a self-controlled decision-making function, a user only needs to provide an electroencephalogram intent, and the rest, i.e., the control on the movement of a robotic arm, is implemented by the automatic planning and control of the system, thereby having a small burden on the user and being convenient for application.

2. The present invention combines the visual identification and positioning technology, a brain-computer interface and a robotic arm to realize the effect that a drink selected by a user can be placed anywhere in a certain range.

3. The present invention combines the visual identification and positioning technology, a brain-computer interface and a robotic arm to comprehensively utilize their advantages. Users can select a drink by themselves through the brain-computer interface in the system of the present invention, and then through the robotic arm in the present invention system and the visual identification and positioning technique, the drink selected by the user is positioned, identified, taken and carried to the user's mouth, so as to facilitate paralyzed patients to drink water by themselves, thereby improving the quality of life of the paralyzed patients and improving their ability to live independently.

DETAILED DESCRIPTION OF EMBODIMENTS

Hereafter the present invention will be further described in detail in conjunction with embodiments and accompanying drawings, but the embodiments of the present invention are not limited thereto.

Embodiment 1

Figure 1:
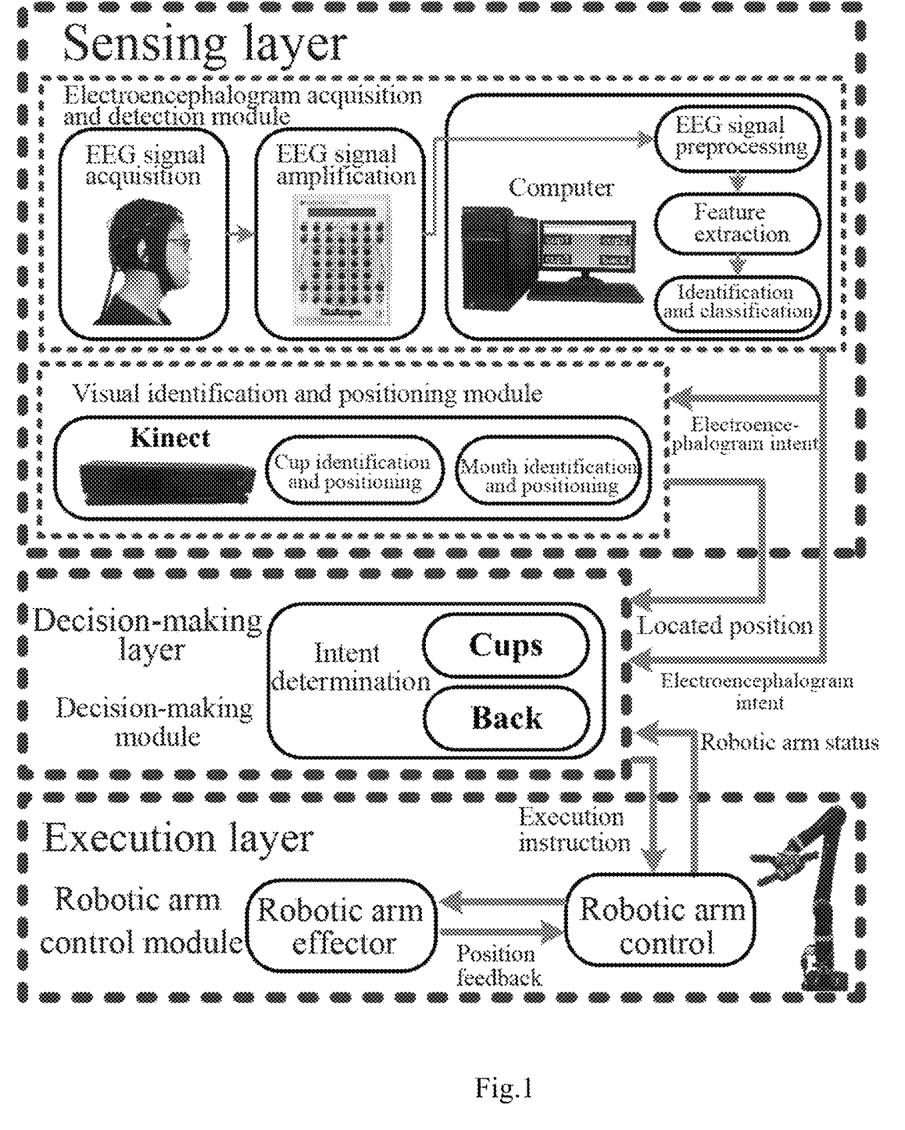
FIG. 1 is a structural block diagram of a brain-computer interface based robotic arm self-assisting system according to the present invention.

As shown in FIG. 1, this embodiment provides a brain-computer interface based robotic arm self-assisting system, which is set up based on a three-layer structure including a sensing layer, a decision-making layer and an execution layer, wherein the sensing layer comprises an electroencephalogram acquisition and detection module and a visual identification and positioning module, the electroencephalogram acquisition and detection module being used for acquiring an electroencephalogram signal and analyzing and identifying the intent of a user, and the visual identification and positioning module being used for identifying and locating positions of a corresponding cup and the user's mouth based on the user intent; the execution layer comprises a robotic arm control module, which is a carrier assisting in operation of a person in practice and performs trajectory planning and control for a robotic arm based on an execution instruction received from a decision-making module; and the decision-making layer comprises a decision-making module, which is connected to the electroencephalogram acquisition and detection module, the visual identification and positioning module and the robotic arm control module to implement acquisition and transmission of data, such as an electroencephalogram signal, a located position and a robotic arm status, and the sending of the execution instruction for the robotic arm.

The electroencephalogram acquisition and detection module comprises an electrode cap for electroencephalogram acquisition, an electroencephalogram acquisition device and a first computer, wherein ten channels of "A1", "T5", "P3", "PZ", "P4", "T6", "O1", "Oz", "O2" and "A2" in the electrode cap are used and disposed at positions according to an international standard 10-20 system; and the first computer is used to implement P300 signal detection and a flickering visual stimulation of a function key in the screen, and the function keys for the flickering visual stimulation are regularly distributed in a 2*2 array in the computer screen, including function keys of "cup1", "cup2", "cup3" and "back", and flicker at an interval of 200 ms with change in black and green colors in a random sequence.

The visual identification and positioning module comprises two Microsoft Kinect vision sensors and a second computer, wherein the two Microsoft Kinect vision sensors are respectively disposed in front of a cup to be taken and in front of a user for identification and positioning of the cup to be taken and the user's mouth; and the second computer is used to implement a cup contour detection algorithm, a cup positioning algorithm, a template matching and identification algorithm, and a mouth identification and positioning algorithm.

The decision-making module implements, based on a TCP communication protocol, acquisition and transmission of data of an electroencephalogram intent, a located position and a robotic arm status and the sending of an execution instruction for the robotic arm by defining unified transmission data variables, including a user's electroencephalogram intent and the information of positions of the cup and the mouth and setting up a service code framework for a client and a server.

The robotic arm control module uses a multi-degree-of-freedom robotic arm as an effector.

Figure 2:
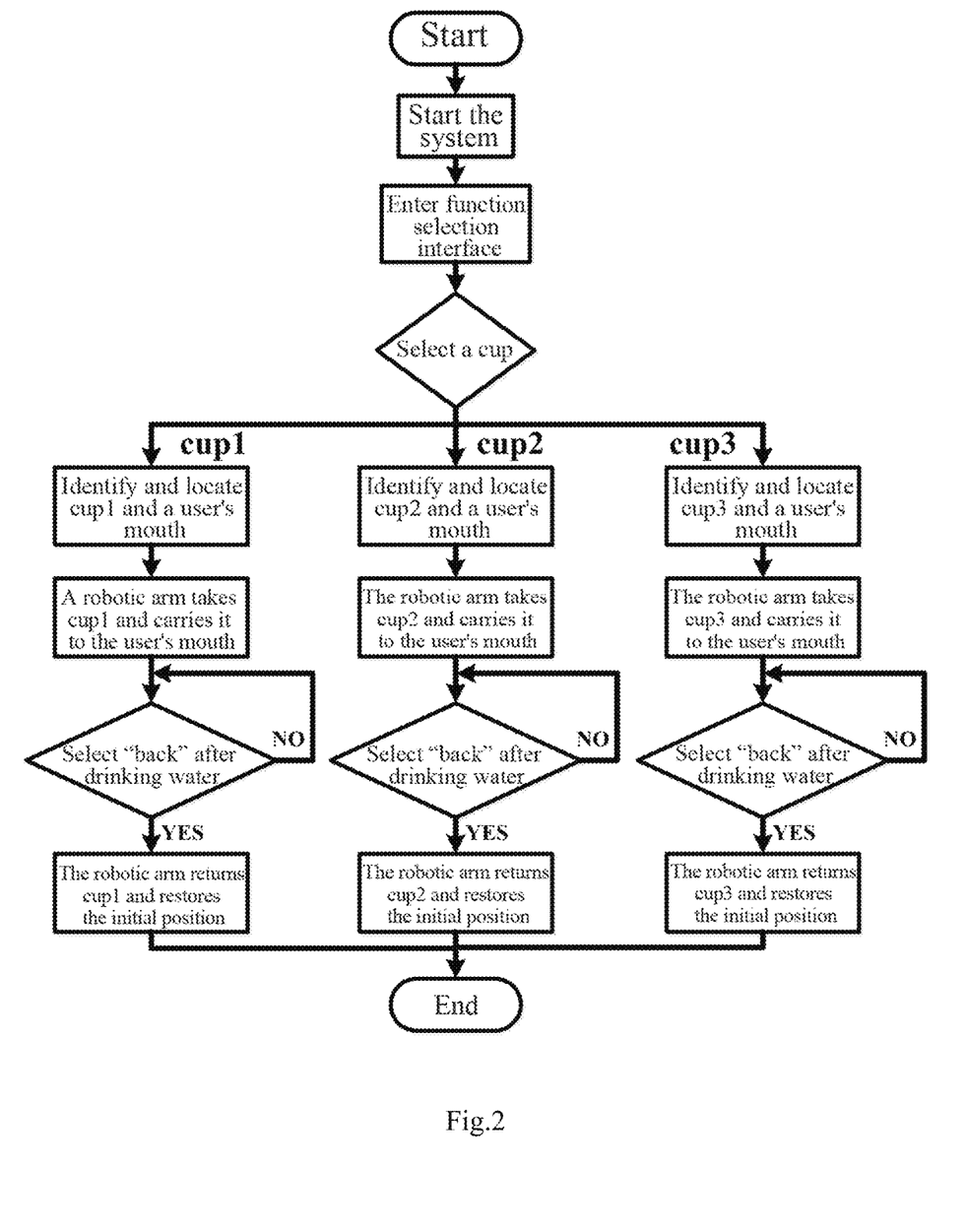
FIG. 2 is a flow chart of a brain-computer interface based robotic arm self-assisting system according to the present invention.

Embodiment 2 this embodiment provides a brain-computer interface based robotic arm self-assisting method, as shown in FIG. 2, the method comprising the steps as follows:

1) a user is sitting in front of a screen of a first computer, adjusts the position thereof, wears an electrode cap for electroencephalogram acquisition, opens an electroencephalogram acquisition device and the first computer, and confirms that the signal acquisition status is good;

2) a brain-computer interface based robotic arm self-assisting system is started to confirm that the Microsoft Kinect vision sensor used for identifying and locating the user's mouth can correctly capture the user's mouth, and confirm that three preset cups to be taken are correctly placed in the field of view of the Microsoft Kinect vision sensor used for identifying and locating the cups to be taken;

3) the screen of the first computer enters a function key interface of flickering visual stimulation, the function key interface comprising four function keys of "cup1", "cup2", "cup3" and "back";

4) the user gazes at one of the three function keys "cup1", "cup2" or "cup3", that is, selecting one of the three preset cups, and once the function key is selected, the electroencephalogram intent of the user about the selection of the cup is obtained and sent to the visual identification and positioning module and the decision-making module;

5) the visual identification and positioning module identifies and locates the position of the corresponding cup and the position of the user's mouth based on the electroencephalogram intent in the step 4) and sends, based on the TCP communication protocol, the information of the positions of the cup selected by the user and the user's mouth to the decision-making module;

6) the decision-making module generates a corresponding execution instruction for the robotic arm based on the information of the positions of the cup and the user's mouth obtained in the step 5) and the electroencephalogram intent obtained in the step 4), and sends the corresponding execution instruction for the robotic arm to the robotic arm control module;

7) the robotic arm control module performs trajectory planning based on the execution instruction for the robotic arm and controls, based on the planned trajectory, the robotic arm to take the cup selected by the user and transfer the cup to the user's mouth;

8) after drinking water, the user gazes at the function key "back", and once the function key is selected, the user's electroencephalogram intent about returning the cup will be obtained and sent to the decision-making module;

9) the decision-making module generates, based on the electroencephalogram intent for returning the cup obtained in the step 8), a corresponding execution instruction for the robotic arm and sends execution instruction for the robotic arm to the robotic arm control module; and 10) the robotic arm control module performs trajectory planning based on the execution instruction for the robotic arm and controls, based on the planned trajectory, the robotic arm to return the cup selected by the user to the original position and restore the initial position status of the robotic arm, so as to realize the self-assisting function of the robotic arm for assisting the user to drink water.

Selecting the function keys in the steps 4) and 8) is specifically implemented by the following process: the user gazes at a certain function key in the function key interface of the first computer, the electroencephalogram signal is acquired, amplified, filtered and processed by analog-to-digital conversion through an electrode cap and an electroencephalogram acquisition device, then the data is transferred to the first computer for P300 signal detection, and then the selection of the certain function key is implemented, the P300 signal detection being specifically implemented by the steps of:

(I) processing the EEG signal by 0.1-20 Hz bandpass filtering and noise reduction; and (II) intercepting, with the amplitude of the EEG signal as a feature, data of a time window of 600 ms after a P300 function key flickers, and performing status classification using a Bayesian model, thereby realizing the P300 signal detection.

Figure 3:
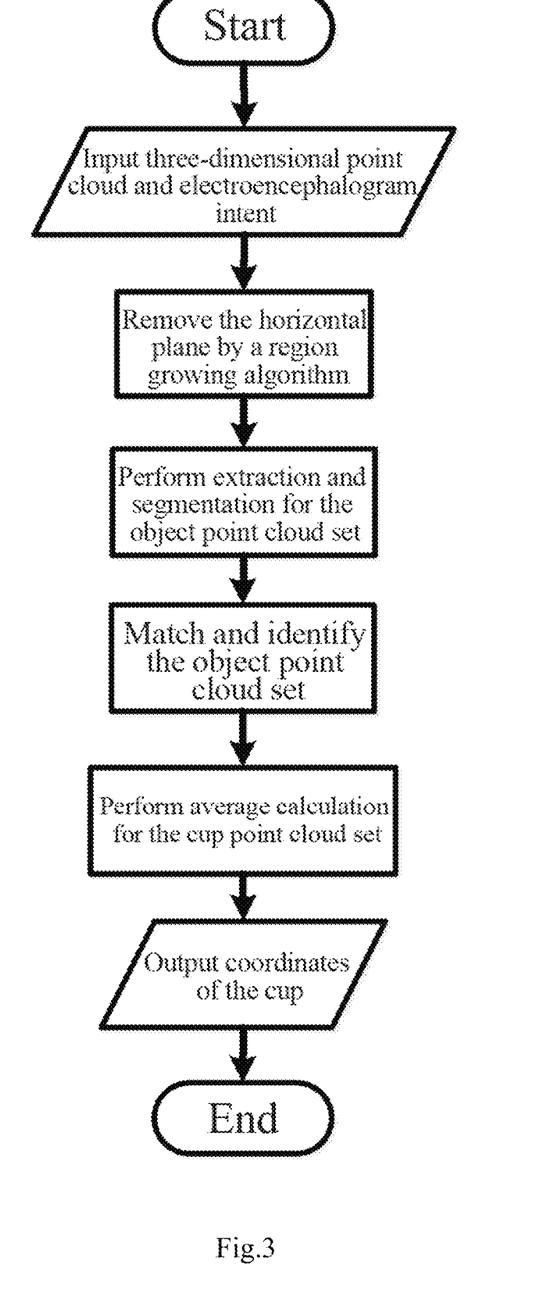
FIG. 3 is a flow chart of identifying and locating the position of a corresponding cup according to the present invention.

In the step 5), as shown in FIG. 3, identifying and locating the position of the corresponding cup is specifically implemented by the steps of:

(1) extracting the horizontal plane in which the cup is placed in the three-dimensional point cloud of the Microsoft Kinect vision sensor through a region growing algorithm;

(2) removing the horizontal plane extracted in the step (1), and performing extraction and segmentation for the object from the remaining three-dimensional point cloud;

(3) respectively matching, using a template matching algorithm, the color image corresponding to each object point cloud set obtained in the step (2) with preset images in a library to identify the point cloud set corresponding to the cup selected by the user; and (4) performing average calculation for the point cloud set corresponding to the selected cup obtained in the step (3) so that the positioning for the cup in a coordinate system of the Microsoft Kinect vision sensor is implemented and converted into the positioning in a robotic arm coordinate system.

In the step 5), identifying and locating the position of the user's mouth is specifically implemented by the steps of: performing human body detection using a software development kit provided by the Microsoft Kinect vision sensor itself so that a coordinate position of the user's mouth in a coordinate system of the Microsoft Kinect vision sensor is acquired and converted into coordinate positions in a robotic arm coordinate system.

Figure 4:
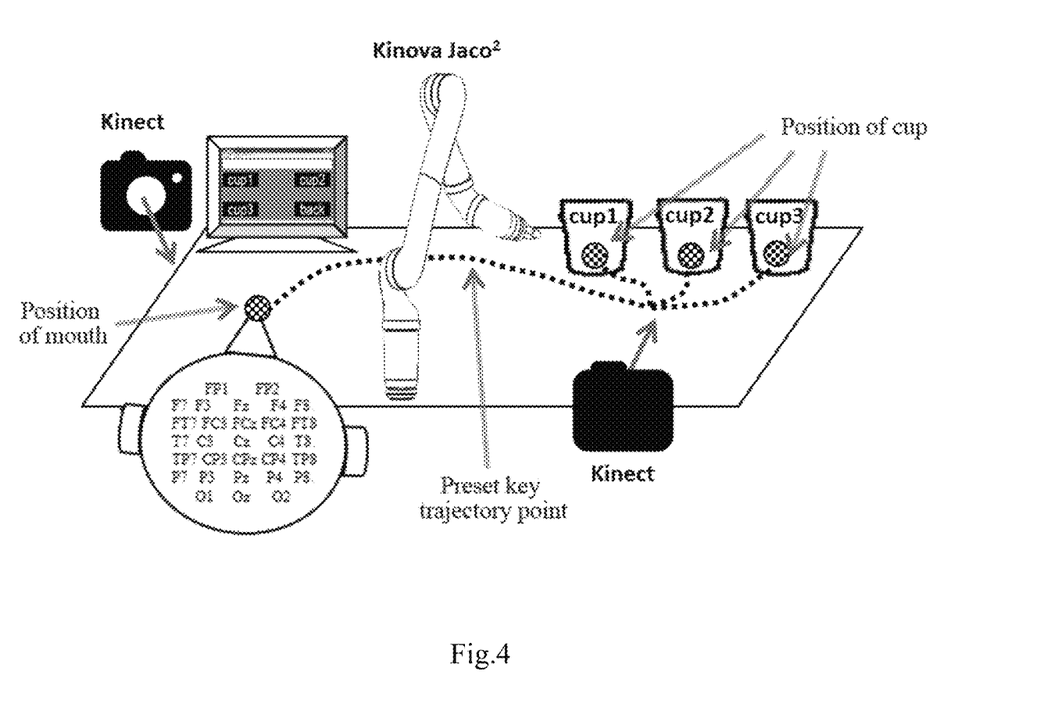
FIG. 4 is a schematic diagram of trajectory planning and control for a robotic arm according to the present invention.

In the steps 7) and 10), as shown in FIG. 4, the trajectory planning and control for the robotic arm is specifically implemented by the process of: combining preset key trajectory points with coordinate points of the user's mouth and the selected cup in the robotic arm coordinate system to plan an operation trajectory of the robotic arm, and calling the corresponding API of the robotic arm to control the robotic arm to operate based on the planned trajectory, so as to realize the self-assisting function of the robotic arm for assisting the user to drink water.

The above description is merely of preferred embodiments of the present invention, but the scope of protection of the present invention is not limited thereto, and any equivalent replacement or variation that can be achieved by a person skilled in the art according to the technical solutions of the present invention patent and the inventive concept thereof in the scope disclosed by the present invention should fall within the scope of protection of the present invention.

The invention claimed is:

1. A robotic arm self-assisting system based on brain-computer interface, characterized in that the system is set up based on a three-layer structure including a sensing layer, a decision-making layer and an execution layer, wherein the sensing layer comprises an electroencephalogram acquisition and detection module and a visual identification and positioning module, the electroencephalogram acquisition and detection module being used for acquiring an electroencephalogram signal and analyzing and identifying an intent of a user, and the visual identification and positioning module being used for identifying and locating positions of a cup and the user's mouth based on the intent; the execution layer comprises a robotic arm control module, the robotic arm control module performs trajectory planning and control for a robotic arm based on an execution instruction received from a decision-making module; and a decision-making layer comprises the decision-making module, the decision-making module is connected to the electroencephalogram acquisition and detection module, the visual identification and positioning module and the robotic arm control module to implement an acquisition and a transmission of data of the electroencephalogram signal, a located position and a robotic arm status, and a sending of the execution instruction for the robotic arm.

2. The robotic arm self-assisting system based on brain-computer interface according to claim 1, characterized in that the electroencephalogram acquisition and detection module comprises an electrode cap for an electroencephalogram acquisition, an electroencephalogram acquisition device and a first computer, wherein ten channels of "A1", "T5", "P3", "PZ", "P4", "T6", "O1", "Oz", "O2" and "A2" in the electrode cap are used and disposed at positions according to an international standard 10-20 system; and the first computer is used to implement a P300 signal detection and a flickering visual stimulation of a function keys in a screen, and the function keys for the flickering visual stimulation are regularly distributed in a 2*2 array in the screen, including function keys of "cup1", "cup2", "cup3" and "back", and the flickering visual stimulation flickers at an interval of 200 ms with a change in black and green colors in a random sequence.

3. The robotic arm self-assisting system based on brain-computer interface according to claim 1, characterized in that the visual identification and positioning module comprises two Microsoft Kinect vision sensors and a second computer, wherein the two Microsoft Kinect vision sensors are respectively disposed in front of a cup to be taken and in front of the user for identification and positioning of the cup to be taken and the user's mouth; and the second computer is used to implement a cup contour detection algorithm, a cup positioning algorithm, a template matching and identification algorithm, and a mouth identification and positioning algorithm.

4. The robotic arm self-assisting system based on brain-computer interface according to claim 1, characterized in that the decision-making module implements, based on a TCP communication protocol, the acquisition and transmission of data of the electroencephalogram intent, the located position and the robotic arm status and the sending of the execution instruction for the robotic arm, by defining unified transmission data variables, including the intent and information of positions of the cup and the mouth and setting up a client-server service code framework.

5. The robotic arm self-assisting system based on brain-computer interface according to claim 1, characterized in that the robotic arm control module uses a multi-degree-of-freedom robotic arm as an effector.

6. A robotic arm self-assisting method based on brain-computer interface, characterized in that the method comprises the steps as follows:
   1) a user sits in front of a screen of a first computer, adjusts a position thereof, wears an electrode cap for an electroencephalogram acquisition, opens an electroencephalogram acquisition device and the first computer, and confirms that a signal acquisition status is good;
   2) a brain-computer interface based robotic arm self-assisting system is started to confirm that a Microsoft Kinect vision sensor used for identifying and locating the user's mouth can correctly capture a user's mouth, and confirm that three preset cups to be taken are correctly placed in a field of view of the Microsoft Kinect vision sensor used for identifying and locating cups to be taken;
   3) the screen of the first computer enters a function key interface of a flickering visual stimulation, the function key interface comprising four function keys of "cup1", "cup2", "cup3" and "back";
   4) the user gazes at one of the three function keys "cup1", "cup2" or "cup3", that is, selecting one of the three preset cups, and once a function key is selected, an intent of the user about a selection of a cup is obtained and sent to a visual identification and positioning module and a decision-making module;
   5) the visual identification and positioning module identifies and locates a position of the cup and a position of the user's mouth based on the intent in the step 4) and sends, based on a TCP communication protocol, information of the positions of the cup selected by the user and the user's mouth to the decision-making module;
   6) the decision-making module generates a corresponding execution instruction for the robotic arm based on the information of the positions of the cup and the user's mouth obtained in the step 5) and the intent obtained in the step 4), and sends the corresponding execution instruction for the robotic arm to a robotic arm control module;
   7) the robotic arm control module performs a trajectory planning based on the execution instruction for the robotic arm and controls, based on a planned trajectory, the robotic arm to take the cup selected by the user and transfer the cup to the user's mouth;
   8) after drinking water, the user gazes at the function key "back", and once the function key is selected, an intent about returning the cup will be obtained and sent to the decision-making module;
   9) the decision-making module generates, based on the intent for returning the cup obtained in the step 8), a corresponding execution instruction for the robotic arm, and sends the corresponding execution instruction for the robotic arm to the robotic arm control module; and
   10) the robotic arm control module performs a trajectory planning based on the execution instruction for the robotic arm and controls, based on a planned trajectory, the robotic arm to return the cup selected by the user to an original position and restore an initial position status of the robotic arm, so as to realize a self-assisting function of the robotic arm for assisting the user to drink water.

7. The robotic arm self-assisting method based on brain-computer interface according to claim 6, characterized in that selecting the function keys in the steps 4) and 8) is specifically implemented by the following process: the user gazes at a certain function key in the function key interface of the first computer, an electroencephalogram signal is acquired, amplified, filtered and processed by an analog-to-digital conversion through an electrode cap and an electroencephalogram acquisition device, then data is transferred to the first computer for a P300 signal detection, and then a selection of the certain function key is implemented, the P300 signal detection being specifically implemented by the steps of:
   (I) processing an EEG signal by a 0.1-20 Hz bandpass filtering and noise reduction; and
   (II) intercepting, with an amplitude of the EEG signal as a feature, data of a time window of 600 ms after a P300 function key flickers, and performing a status classification using a Bayesian model, thereby realizing the P300 signal detection.

8. The robotic arm self-assisting method based on brain-computer interface according to claim 6, characterized in that in the step 5), identifying and locating the position of the cup is specifically implemented by the steps of:

(1) extracting a horizontal plane in which the cup is placed in a three-dimensional point cloud of the Microsoft Kinect vision sensor through a region growing algorithm;
(2) removing the horizontal plane extracted in the step (1), and performing an extraction and a segmentation for an object from a remaining three-dimensional point cloud;
(3) respectively matching, using a template matching algorithm, a color image corresponding to each object point cloud set obtained in the step (2) with preset images in a library to identify a point cloud set corresponding to the cup selected by the user; and
(4) performing an average calculation for the point cloud set corresponding to the selected cup obtained in the step (3) so that a positioning for the cup in a coordinate system of the Microsoft Kinect vision sensor is implemented and converted into a positioning in a robotic arm coordinate system.

9. The robotic arm self-assisting method based on brain-computer interface according to claim 6, characterized in that in the step 5), identifying and locating the position of the user's mouth is specifically implemented by the steps of: performing a human body detection using a software development kit provided by the Microsoft Kinect vision sensor itself so that a coordinate position of the user's mouth in a coordinate system of the Microsoft Kinect vision sensor is acquired and converted into coordinate positions in a robotic arm coordinate system.

10. The robotic arm self-assisting method based on brain-computer interface according to claim 6, characterized in that in the steps 7) and 10), performing the trajectory planning and control for the robotic arm is specifically implemented by: combining preset key trajectory points with coordinate points of the user's mouth and the selected cup in a robotic arm coordinate system to plan an operation trajectory of the robotic arm, and calling a corresponding API of the robotic arm to control the robotic arm to operate based on the planned trajectory, so as to realize the self-assisting function of the robotic arm for assisting the user to drink water.

* * * * *

UNITED STATES PATENT AND TRADEMARK OFFICE
CERTIFICATE OF CORRECTION

| | | |
|---|---|---|
| PATENT NO. | : 11,602,300 B2 | Page 1 of 1 |
| APPLICATION NO. | : 16/471505 | |
| DATED | : March 14, 2023 | |
| INVENTOR(S) | : Zhijun Zhang et al. | |

It is certified that error appears in the above-identified patent and that said Letters Patent is hereby corrected as shown below:

In the Claims

Column 9, Line 15, delete "of a function keys" and insert --of function keys--

Column 10, Line 16, delete "of the positions" and insert --of the position--

Signed and Sealed this
Sixth Day of June, 2023

Katherine Kelly Vidal
*Director of the United States Patent and Trademark Office*